United States Patent [19]

Cooley et al.

[11] 4,011,944

[45] Mar. 15, 1977

[54] DISPOSABLE SURGICAL EQUIPMENT TRAY

[75] Inventors: Denton A. Cooley; Charles C. Reed, both of Houston; Russell G. Sharp, Sugar Land, all of Tex.

[73] Assignee: Texas Medical Products, Inc., Houston, Tex.

[22] Filed: Nov. 17, 1975

[21] Appl. No.: 632,337

[52] U.S. Cl. .................. 206/557; 206/370; 206/523; 220/65; 229/2.5 R

[51] Int. Cl.² .................. B65D 1/34; B65D 25/14

[58] Field of Search ........... 206/72, 350, 370, 523; 229/2.5, 14 C; 220/69, 70, 23.4, 65

[56] References Cited

UNITED STATES PATENTS

| | | | |
|---|---|---|---|
| 3,009,291 | 11/1961 | Blackmore | 220/23.4 |
| 3,285,409 | 11/1966 | Loran | 206/72 |
| 3,468,468 | 9/1969 | Foote | 229/2.5 |
| 3,804,239 | 4/1974 | O'Brien | 206/523 |
| 3,868,016 | 2/1975 | Szpur et al. | 206/350 |

*Primary Examiner*—William T. Dixson, Jr
*Attorney, Agent, or Firm*—H. Ross Workman; J. Winslow Young

[57] ABSTRACT

A surgical equipment tray inexpensively fabricated from a sheet of rigid plastic material. The tray has an absorbent, lint-free surface which (1) absorbs fluids, (2) provides a nonskid instrument surface, and (3) attenuates the noises associated with handling instruments on the tray. Longitudinal ridges and grooves may be included in the base of the tray to provide rigidity to the tray and elevate or expose the instruments for easy access.

1 Claim, 4 Drawing Figures

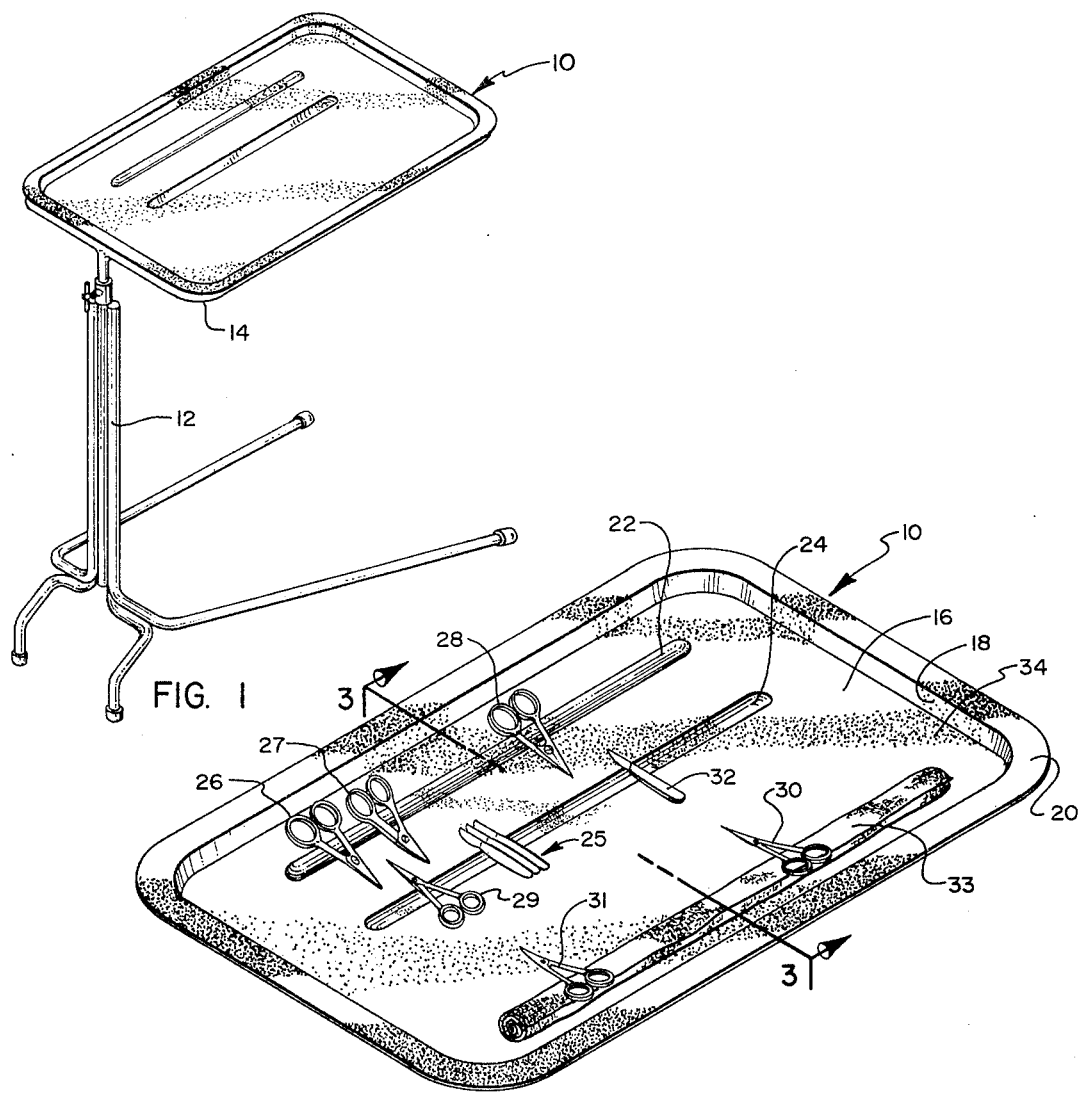
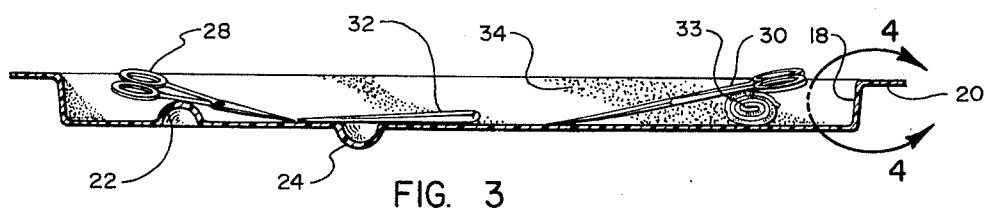
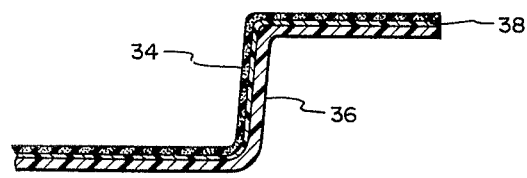

DISPOSABLE SURGICAL EQUIPMENT TRAY

BACKGROUND

1. Field of the Invention

This invention relates to surgical equipment trays.

2. The Prior Art

Surgical equipment trays are available in a variety of sizes and are used to display, for ready access, the surgical equipment used by surgical personnel during a surgical procedure. Conventional trays are fabricated from metal, usually stainless steel, and cannot be economically disposed of but must be suitably cleansed and sterilized before being reused.

Surgical equipment trays are designed to be supported on stands which are placed adjacent the operating area in an operating room. One common tray is referred to in the art as the Mayo tray and is specifically designed to be supported by a Mayo Stand, and, more particularly, to nest within a framework on the Mayo Stand known as the Mayo Stand Ring.

Conventionally, a metal tray is prepared by having its flat base covered with a sterile cloth towel. The cloth provides the necessary absorbent surface and also partially attenuates noises made by contact between the steel instruments and the steel tray. A second sterile towel is hand rolled and placed on the covered tray to form a raised ridge. Sterile surgical instruments and equipment are arrayed on the cloth surface and elevated by the rolled towel ridge according to the type of surgical procedure being performed and the individual preferences of the particular surgeon. The ridge elevates the instruments to permit an orderly leafed array of the instruments for storage convenience and ready hand access of the instruments.

Cloth towels are useful for the foregoing reasons. However, cloth towels are also a source of lint which is undesirable for most surgical procedures and is intolerable for many types of microsurgical procedures. Additionally, cloth towels are not ironed and, therefore, form a wrinkled, uneven surface on the steel tray. Cloth towels also provide very little frictional resistance in association with metal trays thereby permitting the load of surgical instruments to readily shift about when the tray is moved or jarred. Furthermore, cloth towels require additional preparation time to suitably drape the tray surface and to roll as an instrument support.

In view of the foregoing, it is desirable to provide a surgical equipment tray which may be inexpensively fabricated from a nonmetallic, sterilizable material which has an absorbent surface incorporated on the tray. Desirably, the tray should include ridges and/or grooves in its base to provide rigidity to the tray and, coincidentally, provide instrument elevating and access features in the tray. Such an invention is disclosed and claimed herein.

BRIEF SUMMARY AND OBJECTS OF THE INVENTION

The present invention is an inexpensive surgical equipment tray which is fabricated from a rigid plastic sheet and includes a foraminous surface. Grooves and/or ridges are molded integrally with the tray to lend rigidity to the base of the tray and to elevate the instruments arrayed thereon to provide convenient hand access. The foraminous surface provides (1) an absorbent surface to prevent the migration of fluids on the tray and (2) a nonskid, lint-free surface for the instruments.

It is therefore a primary object of this invention to provide improvements in surgical instrument trays.

It is another object of this invention to provide a surgical instrument tray having instrument supporting features integrally formed therein.

An even still further object of this invention is to provide a surgical equipment tray having a foraminous, lint-free surface.

An even still further object of this invention is to provide an inexpensively produced and, therefore, readily disposable surgical instrument tray.

These and other features and objects of the present invention will become more fully apparent from the following description and appended claims taken in conjunction with the accompanying drawings.

BRIEF DESCRIPTION OF THE DRAWING

FIG. 1 is a perspective illustration of one presently preferred embodiment of the surgical instrument tray of this invention shown in the environment of a conventional Mayo Stand;

FIG. 2 is an enlarged perspective illustration of the surgical instrument tray of FIG. 1;

FIG. 3 is a cross section taken along lines 3—3 of FIG. 2; and

FIG. 4 is an enlargement of section 4—4 of FIG. 3.

DETAILED DESCRIPTION OF THE PREFERRED EMBODIMENTS

The invention is best understood by reference to the figures wherein like parts are designated with like numerals throughout.

Referring now more particularly to FIG. 1, the surgical instrument tray of this invention is shown generally at 10 in cooperation with a conventional Mayo stand 12. The Mayo stand 12 includes a framework 14 which is known as a Mayo Stand Ring. Framework 14 is configurated as a rectangular loop and is adapted to receive tray 10 in a nesting relationship. Mayo stand 12 can, clearly, be any suitable surgical instrument tray stand.

Referring now to FIG. 2, tray 10 includes a base 16, a raised sidewall 18 and lip 20. The dimensions of the periphery of tray 10 including sidewall 18 and lip 20 are configurated such that tray 10 readily nests within the confines of framework 14 (FIG. 1).

Base 16 is a flat surface and, desirably includes surface deformations in the form of ridge 22 and a groove 24 therein to provide (1) rigidity to base 16 and (2) hand access to surgical instrument placed thereon. Any desirable number of ridges 22 and/or grooves 24 may be formed into the base 16. While the base 16 may be entirely flat, the ridges and/or grooves are presently preferred in at least one side of the tray 10, as shown, to lend dimensional stability to the tray and improve instrument access with reduced effort. Preferably, the surface deformations are located parallel to the longest axis of the tray 10 and spaced inwardly from the lip 20. In the illustrated embodiment, base 16 includes a ridge 22 and a groove 24 upon which a plurality of instruments may be arrayed as indicated schematically with instruments 25–32. Surgical instruments 25–32 are shown herein schematically whereas, conventionally, the surgical instruments may be stacked in a leafed or overlapping relationship.

With particular reference to FIG. 3, the relationship between the instruments 25–29 and 32 and ridge 22 and groove 24 is more clearly illustrated to demonstrate the increased accessibility of the instruments. Historically, a rolled cloth towel 33 is placed in tray 10 and serves the same purpose as ridge 22. As stated previously, however, cloth towel 33 requires additional handling and is also a source of lint to the surgical instruments placed thereon. The ridge 22 holds the instrument handles above the flat surface of base 16 for facile hand retrieval. When the instruments are placed across recess 24, each instrument may be easily accessed by placing a finger in the recess beneath the selected instrument.

Tray 10 is fabricated with ridge 22 and groove 24 therein as shown in the left side at FIG. 3 to provide increased dimensional stability to tray 10. On the other hand, one may selectively dispense with ridge 22 and groove 24 as shown in the right side of FIG. 3 to provide a flat surface which accommodates at least one rolled towel 33 in procedures where towel lint is less critical.

Referring now more particularly to FIG. 4, an enlarged section along line 4—4 of FIG. 3 is shown to more clearly illustrate the relationship between body 36 and the foraminous surface 34. The material for the base may be any suitable moldable material having sufficient strength to support the weight of instruments as they are transported from place to place upon the tray 10. High impact styrene about 40 mil thick is presently preferred because it can be easily vacuum molded and readily bonds to conventional foraminous foam materials. Preformed cardboard could also be used. In particular, foraminous surface 34 is bonded to body 36 with an adhesive 38. Preferentially, the foraminous surface 34 is fabricated as a thin sheet of commercially available, organic cellular sponge-like material so as to be (1) lint-free, (2) absorbent, (3) sterilizable and (4) closely conform to the contour of tray 10. While a number of commercially available foraminous materials could be used, thin layer urethane foam has been found acceptable.

Tray 10 may be prepared by obtaining a plastic sheet of tray material for body 36 to which a foraminous surface 34 is bonded and thereafter molding and trimming tray 10. Alternatively, the foraminous surface 34 may be bonded to the contour of tray 10 after tray 10 had been suitably formed. When the foraminous layer is bonded over the sidewall 18 and lip 20, a portion of the instruments may effectively be rested directly upon the lip 20 so as to entirely avoid the need for rolled towels or other supports. Moreover, in this manner the entire periphery of the tray 10 may be used to support instruments accessibly.

Selectively, foraminous surface 34 may be bonded to the entire tray surface or only a discrete section of tray 10, for example, only on those areas where instruments 26–30 are to be placed.

The invention may be embodied in other specific forms without departing from its spirit or essential characteristics. The described embodiments are not to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A tray for surgical instruments comprising:
    a unitary molded tray constructed of rigid plastic and comprising a recessed base, a raised sidewall extending around the entire periphery of the base and a laterally extending lip contiguous with and projecting from the sidewall, the sidewall laterally extending lip configurated to nest within a conventional Mayo stand ring;
    at least one elongated upstanding ridge formed on the unitary molded tray and at least one elongated recess formed in the unitary molded tray, each of the ridge and recess facilitating finger access of instruments placed thereon; and
    a thin layer of organic, cellular, sponge-like material which is absorbent and sterilizeable, the sponge-like material being bonded over the entire exposed upper surface of the tray, including each ridge and recess.

* * * * *

UNITED STATES PATENT AND TRADEMARK OFFICE
CERTIFICATE OF CORRECTION

PATENT NO. : 4,011,944
DATED : March 15, 1977
INVENTOR(S) : DENTON A. COOLEY, CHARLES C. REED, RUSSELL G. SHARP It is certified that error appears in the above-identified patent and that said Letters Patent are hereby corrected as shown below:

Column 4, line 17, delete the word "not".

Signed and Sealed this

Twenty-first Day of June 1977

[SEAL]

Attest:

RUTH C. MASON
*Attesting Officer*

C. MARSHALL DANN
*Commissioner of Patents and Trademarks*